United States Patent
Ben Nun

[11] Patent Number: 6,045,535
[45] Date of Patent: Apr. 4, 2000

[54] SURGICAL SEALING SLEEVE

[75] Inventor: Yehoshua Ben Nun, Vitkin, Israel

[73] Assignee: One Way Ocular Technology Ltd., Ramat Gan, Israel

[21] Appl. No.: 09/202,145

[22] PCT Filed: May 29, 1997

[86] PCT No.: PCT/IL97/00171

§ 371 Date: Dec. 9, 1998

§ 102(e) Date: Dec. 9, 1998

[87] PCT Pub. No.: WO97/47247

PCT Pub. Date: Dec. 18, 1997

[30] Foreign Application Priority Data

Jun. 13, 1996 [IL] Israel ......... 118653
Dec. 12, 1996 [IL] Israel ......... 119813

[51] Int. Cl.⁷ ............... A61M 5/178
[52] U.S. Cl. ............ 604/169; 604/256; 604/264
[58] Field of Search ............ 604/171, 256, 604/264, 163, 164, 167, 169

[56] References Cited

U.S. PATENT DOCUMENTS

| | | |
|---|---|---|
| 3,528,425 | 9/1970 | Banko . |
| 3,902,517 | 9/1975 | Hastwell . |
| 4,000,739 | 1/1977 | Stevens . |
| 4,033,349 | 7/1977 | Baehr . |
| 4,084,606 | 4/1978 | Mittleman . |
| 4,096,860 | 6/1978 | McLaughlin . |
| 4,235,232 | 11/1980 | Spaven et al. . |
| 4,239,042 | 12/1980 | Asai . |
| 4,465,470 | 8/1984 | Kelman . |
| 4,573,979 | 3/1986 | Blake . |
| 4,652,255 | 3/1987 | Martinez . |
| 4,721,133 | 1/1988 | Sundblom . |
| 4,795,426 | 1/1989 | Jones . |
| 4,891,044 | 1/1990 | Mitchell . |
| 4,897,079 | 1/1990 | Zaleski et al. . |
| 4,944,732 | 7/1990 | Russo . |
| 4,983,160 | 1/1991 | Steppe et al. . |
| 5,234,410 | 8/1993 | Graham et al. ........ 604/167 |
| 5,242,412 | 9/1993 | Blake III . |
| 5,250,065 | 10/1993 | Clement et al. . |
| 5,257,973 | 11/1993 | Villasuso . |
| 5,273,751 | 12/1993 | Dubroff . |
| 5,286,256 | 2/1994 | Mackool . |
| 5,306,237 | 4/1994 | Clement et al. . |
| 5,350,360 | 9/1994 | Ensminger et al. . |
| 5,403,264 | 4/1995 | Wohlers . |
| 5,429,609 | 7/1995 | Yoon ........ 604/167 |
| 5,487,725 | 1/1996 | Peyman . |
| 5,545,179 | 8/1996 | Williamson, IV ........ 606/213 |
| 5,634,911 | 6/1997 | Hermann et al. ........ 604/256 |
| 5,683,378 | 11/1997 | Christy ........ 606/1 |
| 5,752,970 | 5/1998 | Yoon ........ 606/185 |
| 5,797,888 | 8/1998 | Yoon ........ 604/280 |

FOREIGN PATENT DOCUMENTS

| | | |
|---|---|---|
| 0 228 185 | 7/1987 | European Pat. Off. . |
| 26 45 520 | 4/1977 | Germany . |
| 9809673 | 3/1998 | WIPO . |

*Primary Examiner*—Corrine McDermott
*Attorney, Agent, or Firm*—Browdy and Neimark

[57] ABSTRACT

A surgical sealing sleeve (1, 32) for preventing undesirable leakage from the humoral fluid filled interior of a mammal organ to an access environment during its temporary seating in an access tissue to the mammal organ. The surgical sealing sleeve (1, 32) has an axially extending rigid tubular sleeve (2) for attachment to the access tissue and having an axially extending passageway (5). The sleeve (2) includes an inner sleeve member (3, 33) nested at least along a portion of its length within an outer sleeve member (4). Each of the inner and outer sleeve members has a proximal end and a distal end, the inner sleeve member (3, 33) having at least one distally directed sheath support member 9(A and 9B, 34) terminating proximal to the distal end of the outer sleeve member. An elastomeric sheath (10) is sealingly interdisposed between the inner and outer sleeve members and distally extending so as to fit over the at least one sheath support member, the elastomeric sheath having an initially sealed end adapted to be cut in situ so as to provide an undirectional slit valve (13A and 13B, 38, normally closed under the pressure prevailing in the mammal organ's interior so as to prevent leakage of its contents therefrom via the passageway to the access environment.

10 Claims, 8 Drawing Sheets

SURGICAL SEALING SLEEVE

FIELD OF THE INVENTION

The present invention is in the field of surgical sealing sleeves for providing temporary access to the interior of a mammal organ in general. In particular, the present invention relates to a surgical sealing sleeve having a unidirectional valve at its distal end for preventing undesirable leakage from a mammal organ's interior to an access environment.

BACKGROUND OF THE INVENTION

Intraocular surgical procedures require three or more sclerotomies for enabling the introduction into an eye's interior of a light probe and a surgical instrument and the connection to either a supply line to a source of pressurized air or an irrigation line to a source of physiological liquid for maintaining normal intraocular pressure despite a continuous undesirable leakage from the eye's interior through the sclerotomies. In view of physiological considerations, the diameter of a sclerotomy is limited to between about 1 mm–1.5 mm.

U.S. Pat. No. 4,795,426 describes a tip portion for a catheter placement cannula, the tip portion being in the form of a pair of flexible lips which assume a naturally flattened shape to provide a seal for preventing the backflow of blood or other fluids. To this end, the lips are made of shape retaining memory material of a relatively thick dimension. In view of such a construction, the tip portion is suitable for insertion into a large access port as made in, for example, an abdominal wall, however, it does not lend itself for miniaturization for insertion into a small access port, for example, a sclerotomy.

SUMMARY OF THE INVENTION

It is an object of the present invention to provide a novel surgical sealing sleeve enabling temporary access to the interior of a mammal organ and having a unidirectional valve at its distal end for preventing undesirable leakage from a mammal organ's interior to an access environment.

In accordance with the teachings of the present invention, there is provided a surgical sealing sleeve for preventing undesirable leakage from the humoral fluid filled interior of a mammal organ to an access environment during its temporary seating in an access tissue to the mammal organ, the surgical sealing sleeve comprising:

(a) an axially extending rigid tubular sleeve for attachment to the access tissue and having an axially extending passageway, said sleeve including an inner sleeve member nested at least along a portion of its length within an outer sleeve member, each of said inner and outer sleeve members having a proximal end and a distal end, said inner sleeve member having at least one distally directed sheath support member terminating proximal to said distal end of said outer sleeve member; and (b) an elastomeric sheath sealingly interdisposed between said inner and outer sleeve members and distally extending so as to fit over said at least one sheath support member, said elastomeric sheath having a a priori sealed end adapted to be cut in situ so as to provide an unidirectional slit valve normally closed under the pressure prevailing in the mammal organ's interior so as to prevent leakage of its contents therefrom via said passageway to the access environment.

The surgical sealing sleeve in accordance with the teachings of the present invention particularly lends itself as an ophthalmic surgical sealing sleeve in that it can be readily miniaturized to a size suitable for insertion into a sclerotomy, e.g., having a diameter in the range of about 1 mm–1.5 mm. However, that notwithstanding, it will be readily appreciated that the surgical sealing sleeve can be adapted for use in large access ports.

The proximal end of the sleeve is preferably formed with an upright projection for releasable insertion into a matching bore in a cutting tool employed for cutting the elastomeric sheath to form the unidirectional slit valve. The projection cum bore ensure that the cutting tool can only cut the elastomeric sheath in a predetermined manner and that the depth of insertion of the cutting tool into the eye is limited to as to prevent infliction of damage to the eye's interior structure.

In addition, the proximal end of the sleeve is preferably formed with an internal screw thread for releasable engagement with an insertion tool employed for manipulating the surgical sealing sleeve prior to a surgical procedure in general and in particular during a sclerotomy and its subsequent removal therefrom.

Due to the lack of elasticity of an eye's sclera, the surgical sealing sleeve is preferably operable as a trocar for puncturing its own sclerotomy, thereby meritoriously reducing leakage between the sclerotomy's rim and the surgical sealing sleeve's outer surface. The projection preferably doubles as an indicating means for indicating the trocar end of the surgical sealing sleeve.

Further objects, features and advantages of the present invention will become apparent from the following detailed description when take in conjunction with the accompanying drawings wherein like reference numerals designate like elements through the several views.

DETAILED DESCRIPTION OF THE INVENTION

Figure 1:
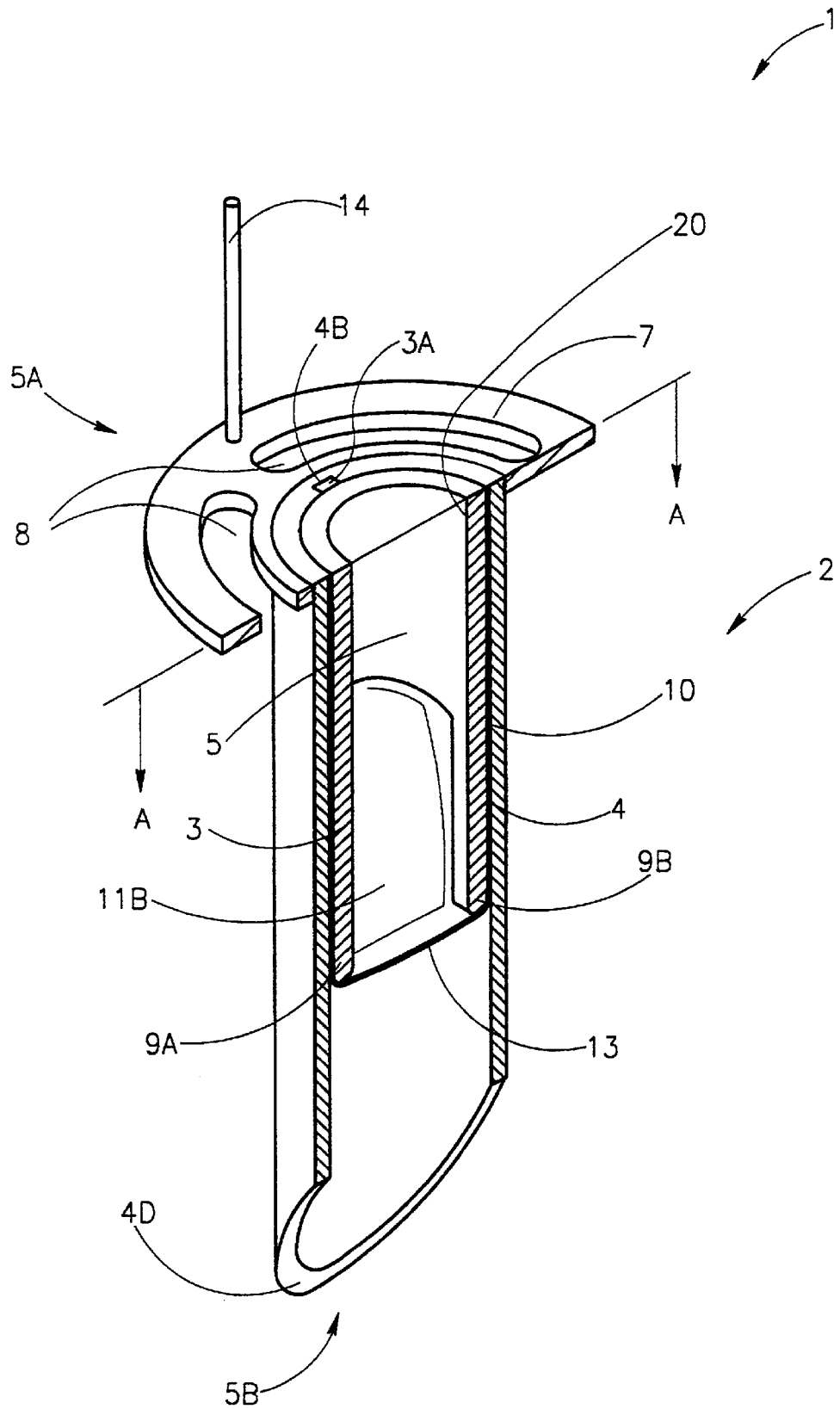
FIG. 1 is a partial cross section perspective view of an assembled surgical sealing sleeve in accordance with a first embodiment of the present invention.
Figure 2:
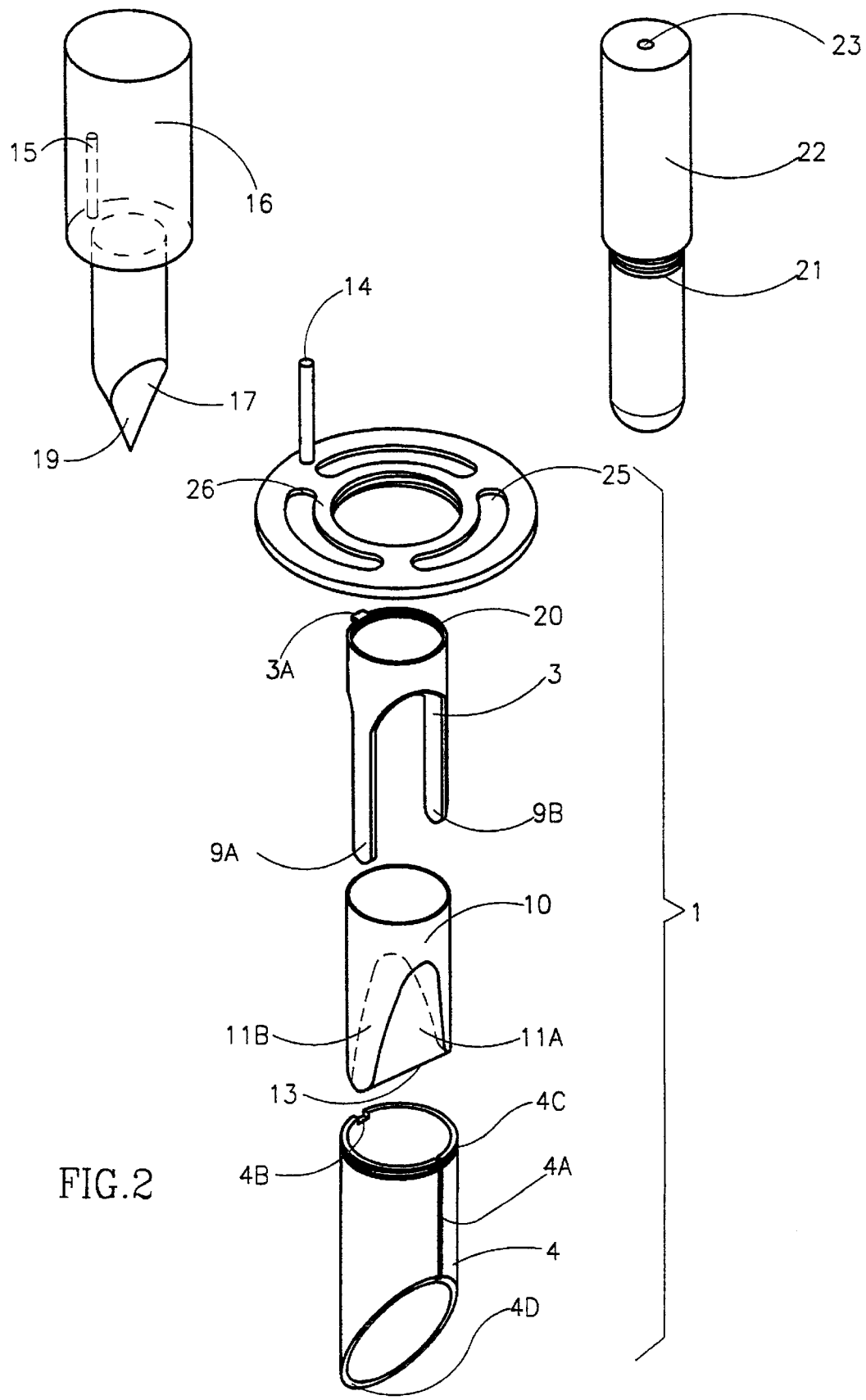
FIG. 2 is an exploded view of the surgical sealing sleeve of FIG. 1 along with its cutting tool and its insertion tool.

With reference now to the drawings, FIGS. 1 and 2 show a surgical sealing sleeve 1 including an axially extending rigid tubular sleeve 2 constituted by an inner sleeve member 3 and an outer sleeve member 4 coaxially disposed therewith and having an axial slit 4A. The sleeve 2 has a passageway 5 axially extending between a proximal end 5A associated with an access environment and a distal end 5B associated with the interior of a mammal eye.

At their proximal ends, the inner sleeve member 3 is formed with a stop 3A adapted for insertion into a matching slot 4B formed in the outer sleeve member 4. In addition, the outer sleeve member 4 is formed with an external screw thread 4C at its proximal end on which is screw threaded an annular fixation plate 7 having two or more apertures 8 enabling suture fixation of the surgical sealing sleeve 1 to an eye's sclera.

At their distal ends, the inner sleeve member 3 is formed with a pair of sheath support members in the form of diametrically opposite axially directed rods 9A and 9B whilst the outer sleeve member 4 is fashioned with a puncturing tip 4D such that the surgical sealing sleeve 1 is operable as trocar. For reasons to become apparent hereinbelow, the tips of the 9A and 9B lie proximal of the puncturing tip 4D and within the full cylindrical portion of the outer sleeve member 4.

On assembly of the surgical sealing sleeve 1, an ultrafine elastomeric sheath 10 of about 0.5 mm thickness and having a sealed sheath end 13 is rolled onto the inner sleeve member 3. The elastomeric sheath 10 is so deployed such that in its relaxed state, its end 13 extends very slightly beyond the tips of the rods 9A and 9B, thereby presenting side walls 11A and 11B converging at a transversely directed sealed sheath end 13.

Thereafter, the outer sleeve member 4 is slightly pried open and the inner sleeve member 3, along with the elastomeric sheath 10 is inserted therein in a distal direction until the stop 3A seats in the slot 4B. Finally, the annular fixation plate 7 is screw threaded onto the outer sleeve member 4 to seal the elastomeric sheath 10 between the inner and outer sleeve member 3 and 4 at the proximal end of the surgical sealing sleeve 1.

The annular fixation plate 7 is formed with an upright projection 14 for releasable insertion in a matching bore 15 formed in a cutting tool 16 having a blade 17 with a wide root tapering to a central stylet tip 19 for initiating the cutting of the sealed sheath end 13. The matching projection 14 and bore 15 are axially dimensioned such that on insertion of the cutting tool 16 into the surgical sealing sleeve 1, the blade 17 cuts along the sealed sheath end 13 between the tips of the rods 9A and 9B so as to form a pair of transversely directed end margins 13A and 13B respectively of side walls 11A and 11B, the end margins 13A and 13B constituting the unidirectional slit valve. Against this, when the bore 15 is not in registration with the projection 14, thereby enabling only the partial insertion of the cutting tool 16 into the surgical sealing device 1, the tool's blade 17 cannot rupture the elastomeric sheath 10.

At its proximal end, the inner sleeve member 3 is formed with an internal screw thread 20 for releasable engagement with a matching external screw thread 21 of a hand held insertion tool 22. The insertion tool 22 is also provided an axially extending lumen 23 to preclude a suction for being developed on its removal from the surgical sealing sleeve 1 which would have a tendency to invert the sealed sheath end 13 into the passageway 5 possibly causing it to rupture.

The insertion tool 22 is axially dimensioned such that on screw engagement with the inner sleeve member 3, its tip bears against the sealed sheath end 13 so as to stretch the elastomeric sheath 10 lengthwise to take up any slack in the side walls 11A and 11B, thereby presenting a smooth contour along the sleeve's entire length such that it can be pushed through a relatively coarse access tissue without it being torn or otherwise damaged. However, at the same time, the insertion tool 22 is axially dimensioned such that the sealed sheath end 13 does not protrude beyond the distal end of the outer sleeve member 4 which would expose the sealed sheath end 13 which then maybe ruptured during a forced insertion through an access tissue.

Figure 3A:
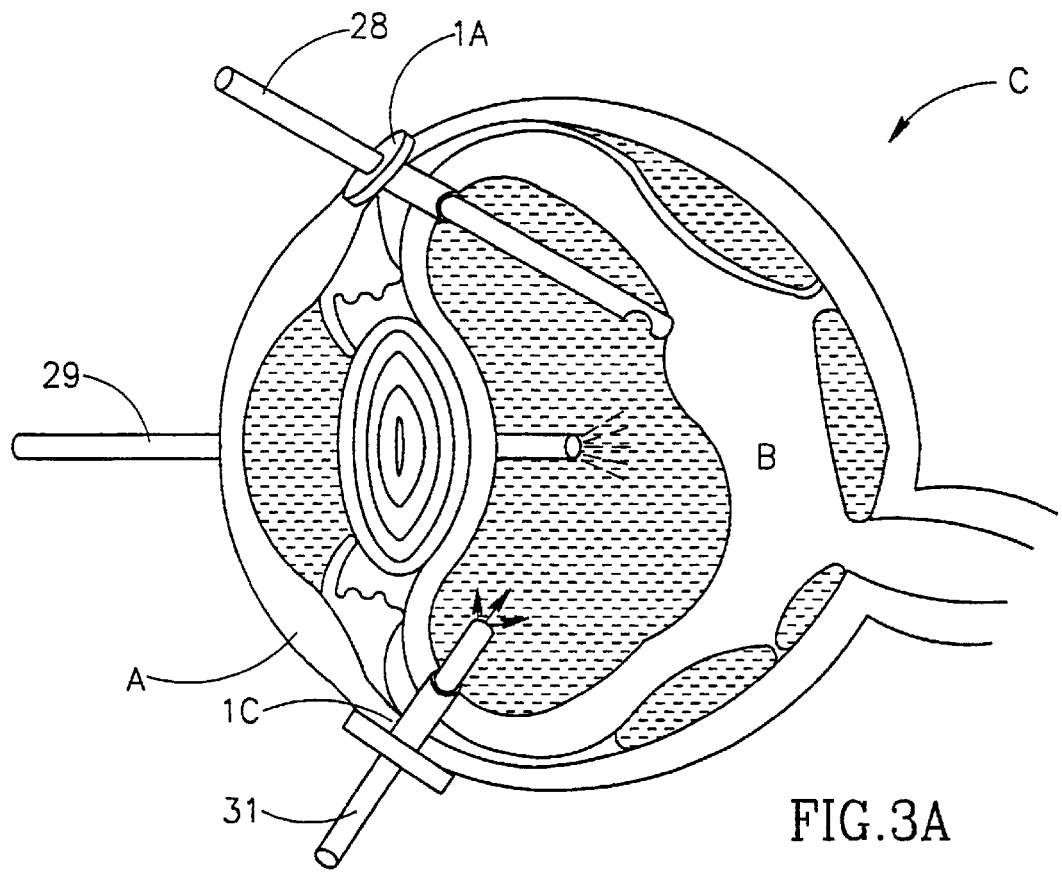
FIGS. 3A and 3B are respectively a schematic cross section side view and a front view of a human eye into whose sclera three surgical sealing sleeves of FIG. 1 have been temporarily inserted.
Figure 3B:
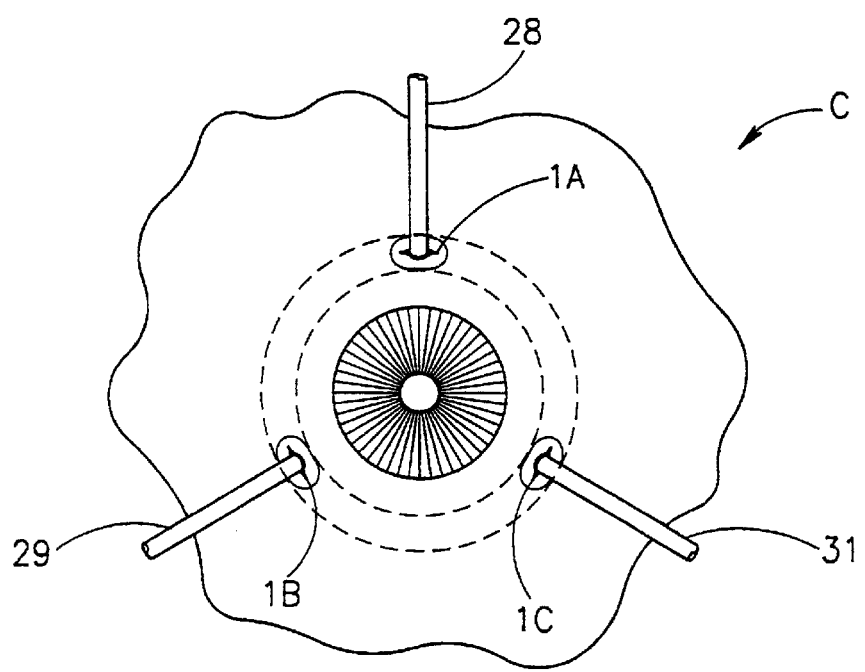

The deployment and use of the surgical sealing sleeve 1 is now described within the context of a sclera-invasive intraocular surgery as schematically shown in FIGS. 3A and 3B in which three surgical sealing sleeves 1A, 1B and 1C have been temporarily inserted into a sclera A of an eye C. As shown, the surgical sealing sleeves 1A, 1B and 1C are respectively employed for enabling the introduction of a surgical instrument 28 and a light source 29 into the eye's vitreous chamber B and connection to an irrigation line 31. Preferably, the light source 29 and the irrigation line 31 are screw threaded into the surgical sealing sleeves 1B and 1C, respectively.

Figure 4:
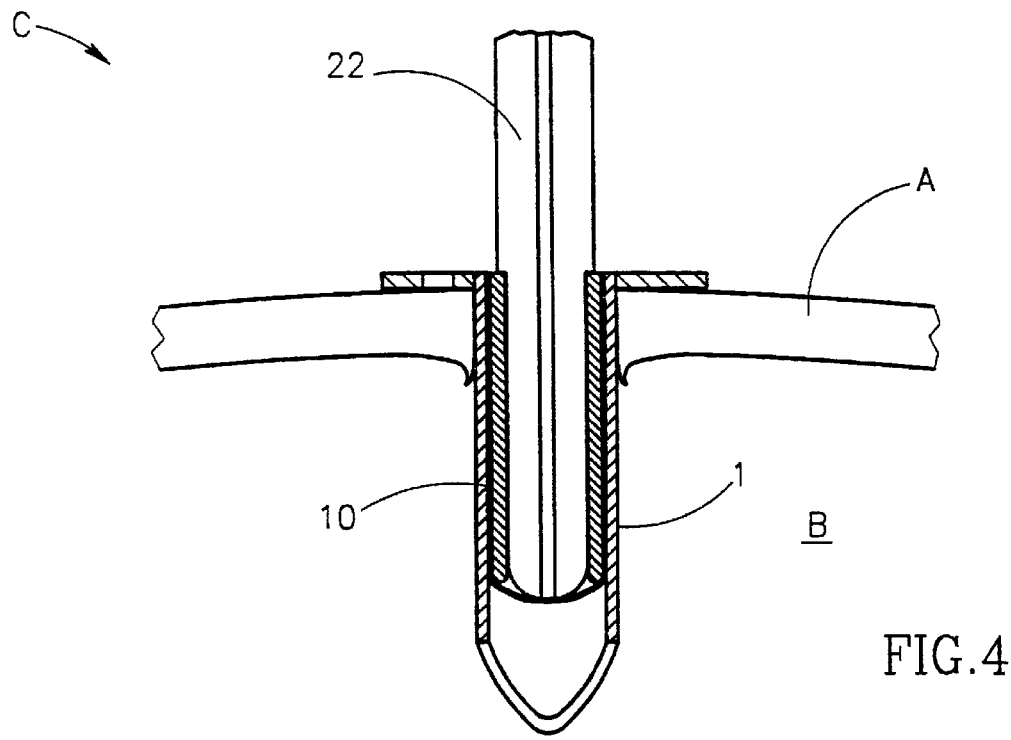
FIG. 4 is a cross section view along line A—A in FIG. 1 showing the insertion of the surgical sealing sleeve into an eye's sclera.
Figure 5:
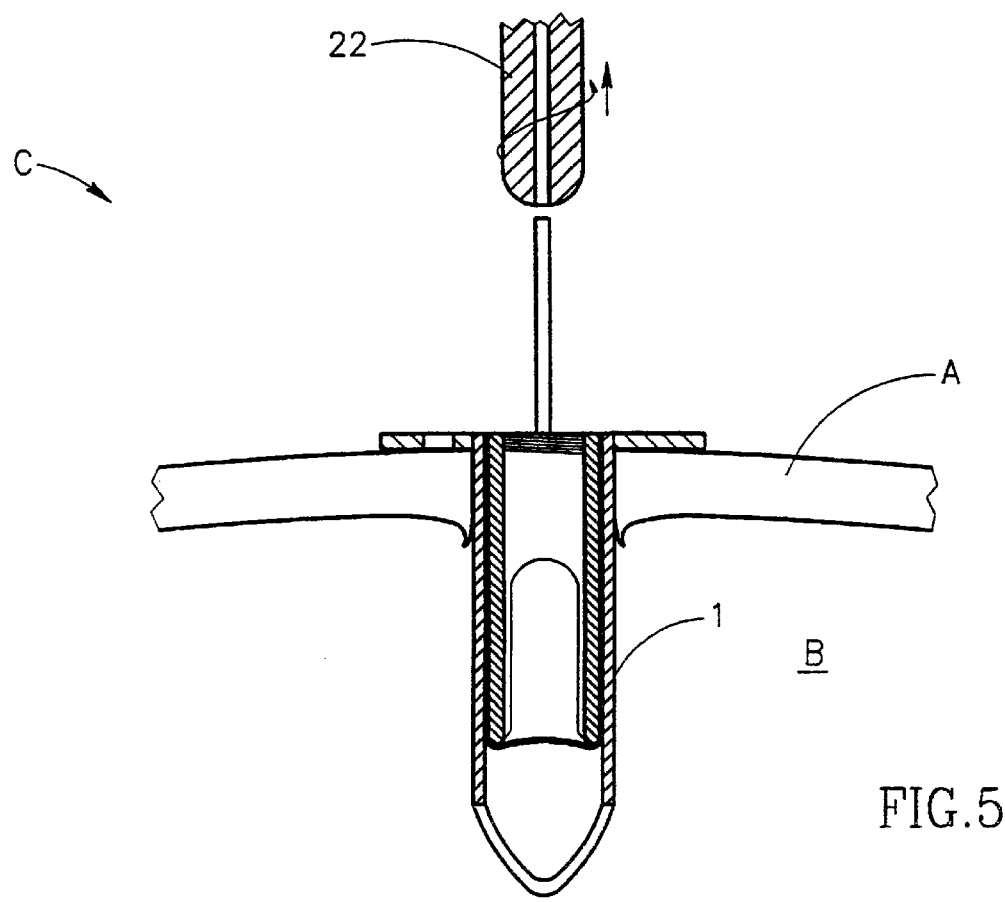
FIG. 5 is a cross section view along line A—A in FIG. 1 showing the removal of the insertion tool from the surgical sealing sleeve.

As shown in FIG. 4, the first stage in the deployment of a surgical sealing sleeve 1, is screwing in the insertion tool 22 such that the surgical sealing sleeve 1 can be hand manipulated for sclerotomy whilst the integrity of its elastomeric sheath 10 is maintained as described hereinabove. During sclerotomy, the projection 14 is used to orient the surgical sealing sleeve 1 such that the puncturing tip 4D does not afflict any damage to an eye's internal structure. As shown in FIG. 5, after suture fixation of the surgical sealing sleeve 1 to sclera A, the insertion tool 22 is unscrewed and removed leaving a still sealed elastomeric sheath 10 which contracts to its original length.

Figure 6:
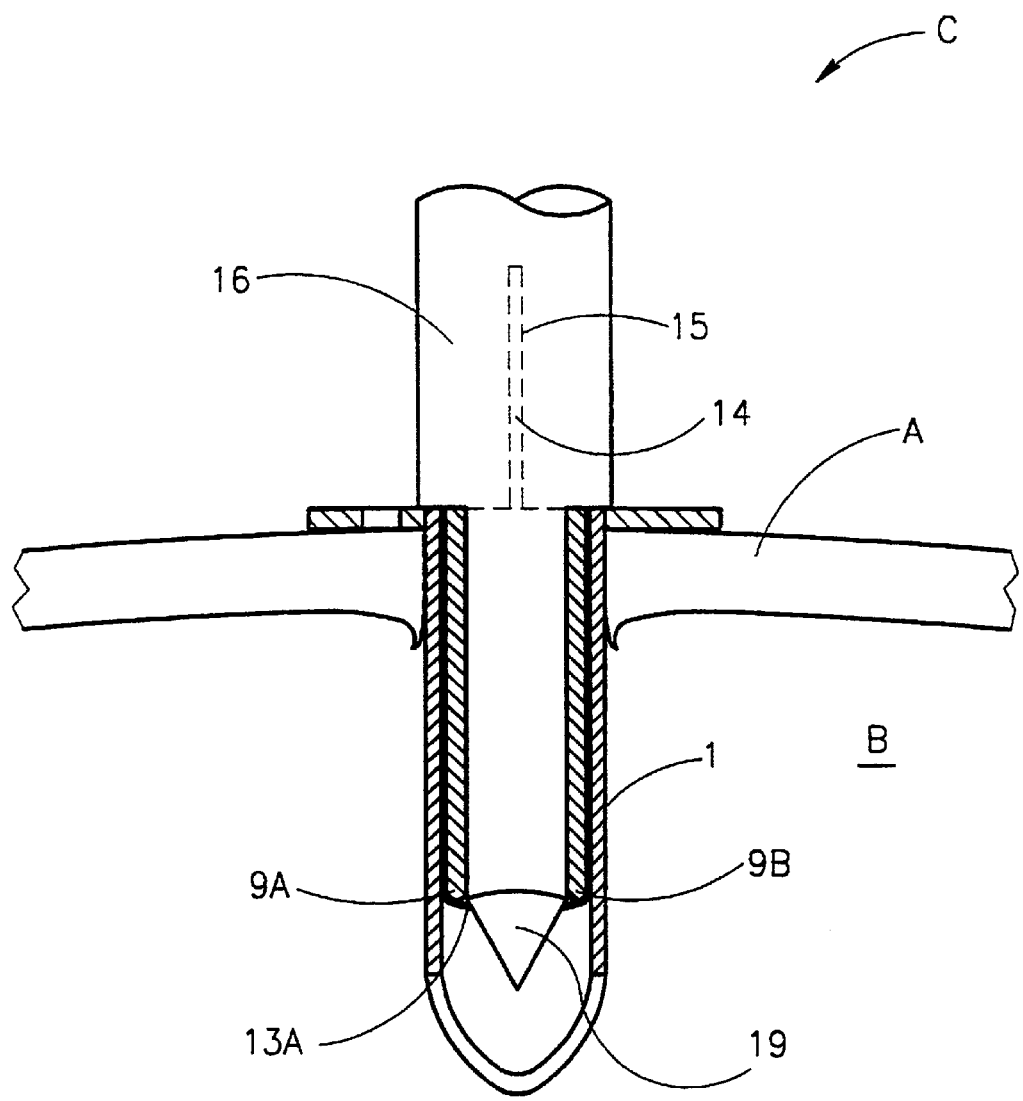
FIG. 6 is a cross section view along line A—A in FIG. 1 showing the cutting of the sheath's sealed end with a cutting tool.
Figure 7:
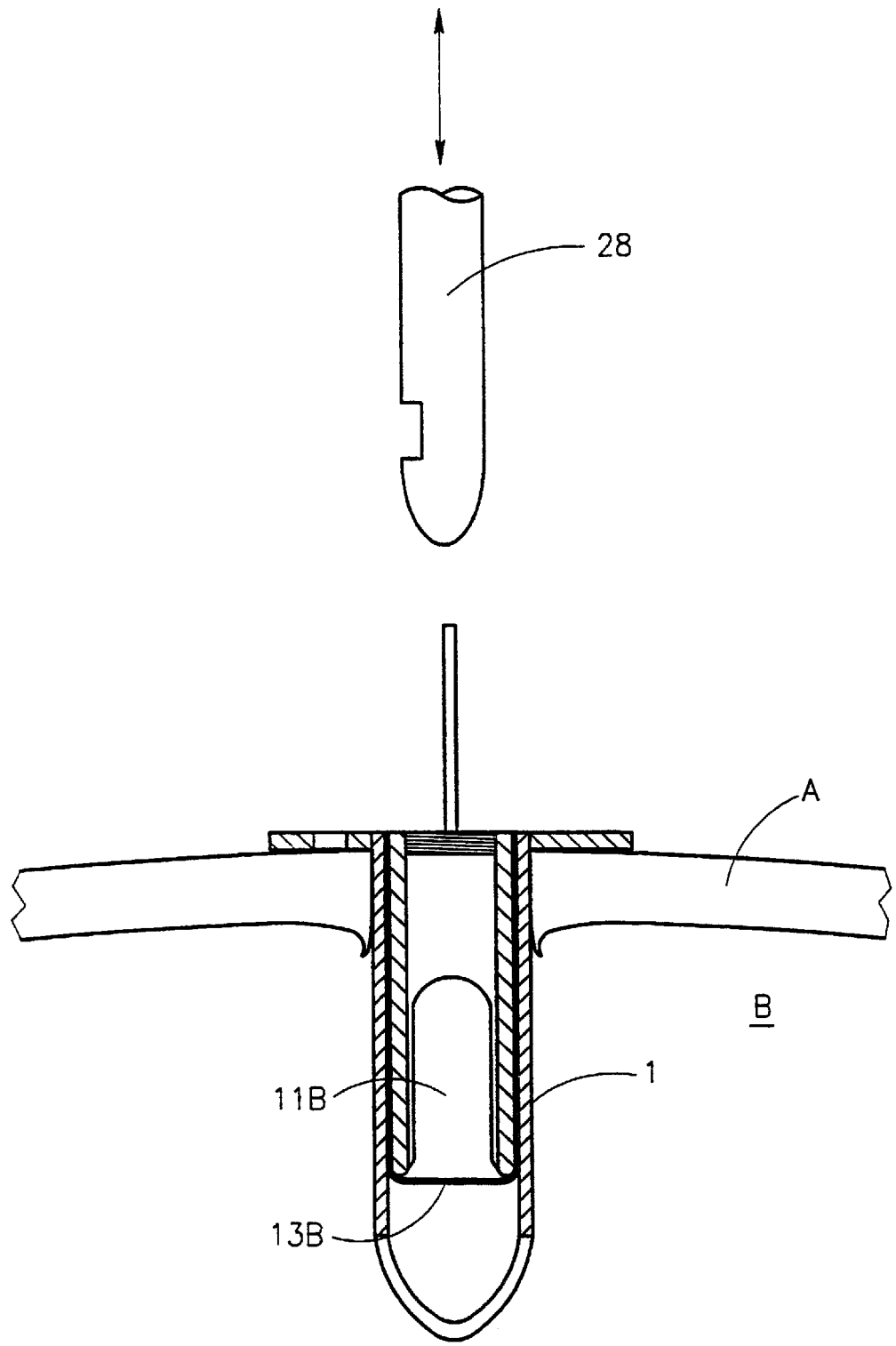
FIG. 7 is a cross section view along line A—A in FIG. 1 showing the sealing action of the surgical sealing sleeve's unidirectional slit valve.

Thereafter, as shown in FIG. 6, the cutting tool 16 is oriented such that its bore 15 is in registration with the sleeve's projection 14 such that on insertion into the surgical sealing sleeve 1, it cuts the sealed sheath end 13 to form the end margins 13A and 13B. On removal of the cutting tool 16, the end margins 13A and 13B seal against one another under the pressure prevailing in the eye's interior, thereby preventing undesirable leakage of intraocular fluid to the exterior whilst at the same time enabling the repeated passage of different surgical instrument into the eye's interior therebetween. The fact that the side walls 11A and 11B distally extend only slightly further than the rods 9A and 9B ensures that the end margins 13A and 13B cannot be inverted and also that they readily part on the passage of a surgical instrument therebetween.

On removal of the surgical sealing sleeve 1 from the eye, by virtue of the distal location of the unidirectional slit valve, a minimal suction force is applied to contents of the vitreous chamber B, thereby minimizing the damage thereto.

Figure 8:
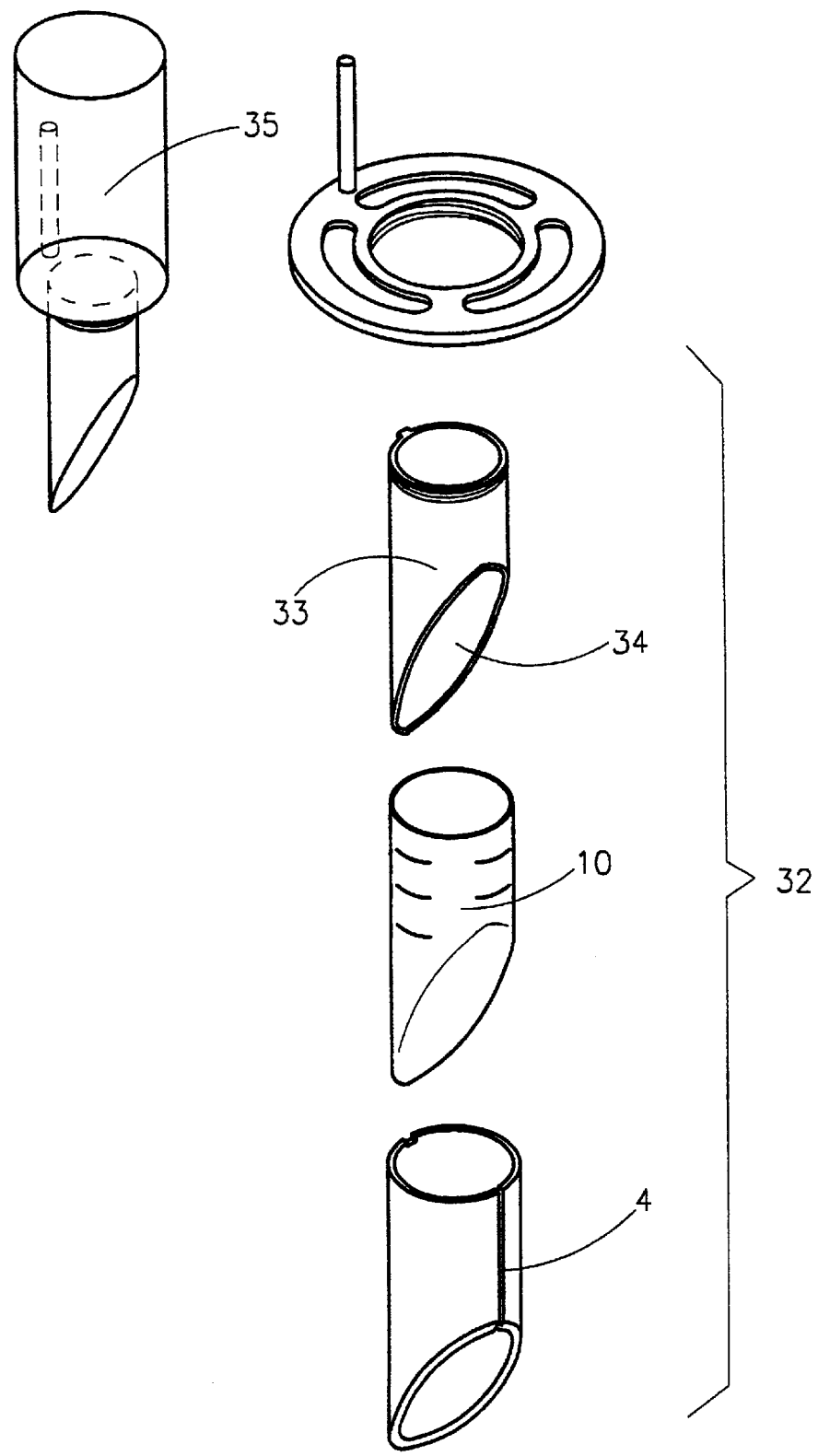
FIG. 8 is an exploded view of a surgical sealing sleeve in accordance with a second embodiment of the present invention.
Figure 9:
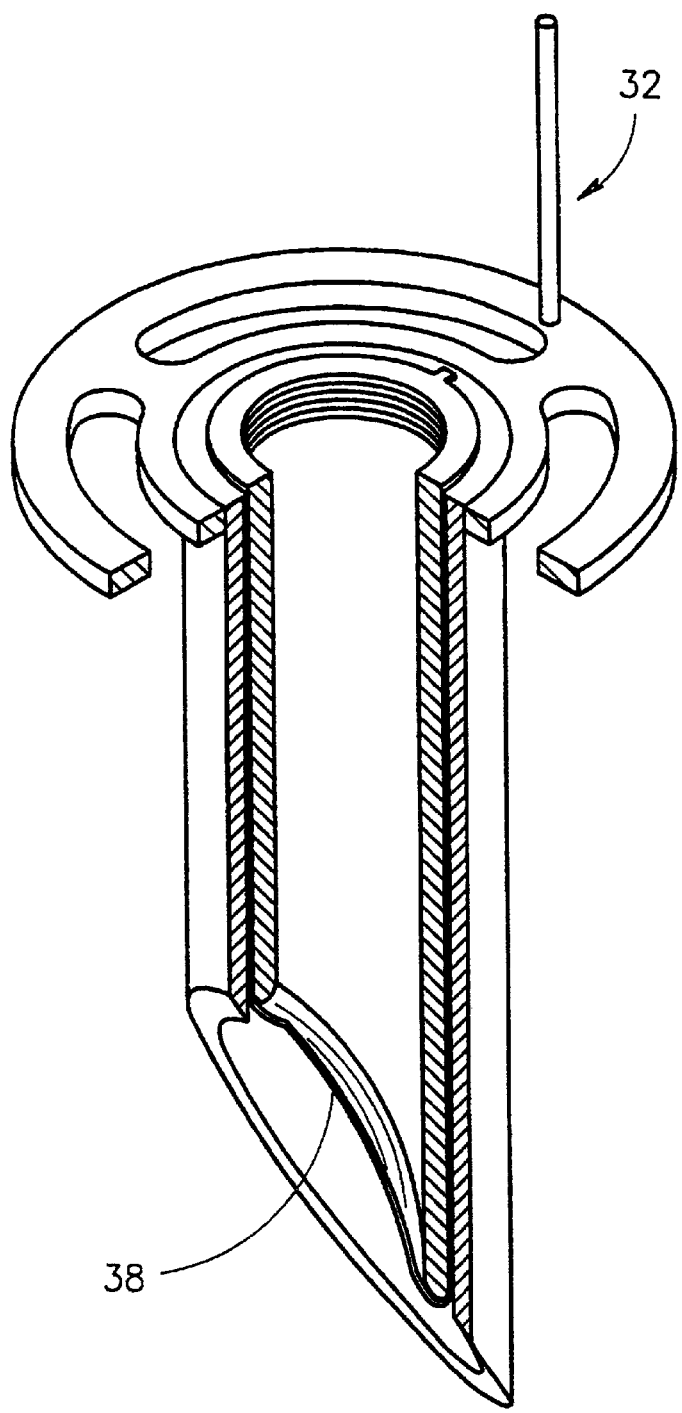
FIG. 9 is a partial cross sectional perspective view of the surgical sealing sleeve of FIG. 8 showing the sealing action of its unidirectional slit valve.

With reference now to FIG. 8, a surgical sealing sleeve 32 is similar to the surgical sealing sleeve 1 except that its inner sleeve member 33 includes a single axially extending, peripherally curved sheath support member 34. The surgical sealing sleeve 32 requires the use of a cutting tool 35 with a stylet tip shaped blade 37 so as to cut the elastomeric sheath 10 to form a sealing flap 38 adapted to seal against the inner surface of the sheath support member 34.

While the invention has been described with respect to a limited number of embodiments, it will be appreciated that many variations, modifications and other applications of the invention may be made.

I claim:

1. A surgical sealing sleeve for preventing undesirable leakage from the humoral fluid filled interior of a mammal organ to an access environment during its temporary seating in an access tissue to the mammal organ, the surgical sealing sleeve comprising:

(a) an axially extending rigid tubular sleeve for attachment to the access tissue and having an axially extending passageway, said sleeve including an outer sleeve member and an inner sleeve member nested at least along a portion of its length within said outer sleeve member, each of said inner and outer sleeve members having a proximal end and a distal end, said inner sleeve member having at least one distally directed sheath support member terminating proximal to said distal end of said outer sleeve member; and (b) an elastomeric sheath sealingly interdisposed between said inner and outer sleeve members and distally extending so as to fit over said at least one sheath support member, said elastomeric sheath having an initially sealed end adapted to be cut in situ so as to provide an unidirectional slit valve normally closed under the pressure prevailing in the mammal organ's interior so as to prevent leakage of its contents therefrom via said passageway to the access environment.

2. A surgical sealing sleeve according to claim 1 wherein the proximal end of the sleeve is provided with an upright projection for releasable insertion in a matching bore of a cutting tool.

3. A cutting tool for use with a surgical sealing sleeve as claimed in claim 2, the cutting tool comprising a blade.

4. A surgical sealing sleeve according to claim 1 wherein the proximal end of the sleeve is provided with an internal screw thread for releasable screw engagement with an insertion tool.

5. An insertion tool for use with a surgical sealing sleeve as claimed in claimed 4, the insertion tool comprising an axially extending body member having an axially extending lumen.

6. A surgical sealing sleeve according to claim 1 wherein the distal end of the sleeve is formed as a trocar.

7. A surgical sealing sleeve according to claim 6 wherein the proximal end of the sleeve is formed with indicating means for indicating the position of the trocar.

8. A surgical sealing sleeve according to claim 7 wherein said indicating means is constituted by a proximally directed projection for releasable insertion in a matching bore of a cutting tool.

9. A surgical sealing sleeve according to claim 1 wherein said unidirectional slit valve includes two transversely directed end margins adapted to seal against one another.

10. A surgical sealing sleeve according to claim 1 wherein said unidirectional slit valve includes a sealing flap adapted to seal against said sheath support member.

* * * * *